(12) United States Patent
Boon et al.

(10) Patent No.: US 7,354,531 B2
(45) Date of Patent: Apr. 8, 2008

(54) POLYMER ELECTROLYTE COMPOSITION

(75) Inventors: Wynham Henry Boon, North Canton, OH (US); Thomas Clayton Forschner, Richmond, TX (US); David Eric Gwyn, Houston, TX (US); James R. MacCallum, St. Andrews (GB); Christopher John Smith, Haslemere (GB); Michael John Smith, Braga (PT)

(73) Assignee: Shell Oil Company, Houston, TX (US)

( * ) Notice: Subject to any disclaimer, the term of this patent is extended or adjusted under 35 U.S.C. 154(b) by 344 days.

(21) Appl. No.: 10/343,804

(22) PCT Filed: Jul. 31, 2001

(86) PCT No.: PCT/EP01/08855

§ 371 (c)(1),
(2), (4) Date: Feb. 18, 2003

(87) PCT Pub. No.: WO02/13298

PCT Pub. Date: Feb. 14, 2002

(65) Prior Publication Data

US 2003/0170546 A1 Sep. 11, 2003

(30) Foreign Application Priority Data

Aug. 4, 2000 (EP) .................................. 00306636

(51) Int. Cl.
*H01B 1/00* (2006.01)
*H01B 1/20* (2006.01)

(52) U.S. Cl. ................ 252/511; 252/182.1; 252/518.2; 252/62.2; 429/304; 429/306; 429/307; 429/317; 526/314; 526/173; 526/181; 526/269; 526/270; 528/354; 528/358; 525/45; 525/411

(58) Field of Classification Search ................ 252/511, 252/510, 519.4; 429/29, 30, 33, 46, 304
See application file for complete search history.

(56) References Cited

U.S. PATENT DOCUMENTS 5,237,031 A * 8/1993 Kubota et al. ............... 526/305

(Continued)

FOREIGN PATENT DOCUMENTS

GB 2143539 A * 2/1985

(Continued)

OTHER PUBLICATIONS

D.E. Fenton, J.M. Parker and P.V. Wright reported the preparation of crystalline complexes of sodium and potassium salts with poly-(ethylene oxide) in Polymer 14 (1973) 589.

(Continued)

*Primary Examiner*—Stanley S. Silverman
*Assistant Examiner*—Kallambella Vijayakumar
(74) *Attorney, Agent, or Firm*—Richard B. Taylor

(57) ABSTRACT

A composition for use as a polymer electrolyte, wherein said composition includes one or more polar materials and one or more polyesters of formula III,

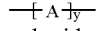
(III)

wherein each unit A may be identical or different and is of the structure IV,

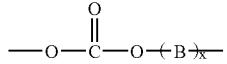
(IV)

wherein each unit B may be identical or different and is of the structure V,

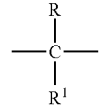
(V)

wherein R and $R^1$ are each, independently, hydrogen, optionally substituted hydrocarbyl or an inert functional group; a process for preparing said composition; the use of said composition as a polymer electrolyte in coulometers, displays, smart windows, cells or batteries; and a cell and/or battery having said composition.

10 Claims, 11 Drawing Sheets

Variation of Conductivity with 1/T for Electrolytes based on the $(TMC)_n$ $LiCF_3SO_3$ System (n = 55 ■, 35 ●, 10 ◆, 9 □ and 7 ○)

U.S. PATENT DOCUMENTS

| | | | | |
|---|---|---|---|---|
| 5,985,487 A | * | 11/1999 | Chaloner-Gill et al. | 429/189 |
| 6,447,952 B1 | * | 9/2002 | Spiegel et al. | 429/218.1 |
| 6,451,949 B2 | * | 9/2002 | Boon et al. | 526/314 |
| 6,471,993 B1 | * | 10/2002 | Shastri et al. | 424/486 |
| 6,562,513 B1 | * | 5/2003 | Takeuchi et al. | 429/189 |
| 6,602,976 B2 | * | 8/2003 | Smith et al. | 528/391 |

FOREIGN PATENT DOCUMENTS

| | | | |
|---|---|---|---|
| JP | 62-254303 | * | 11/1987 |
| JP | 11-060870 | * | 3/1999 |
| JP | 11 060870 | | 3/1999 |
| JP | 2000 086711 | | 3/2000 |
| JP | 2000-086711 | * | 3/2000 |
| WO | 96/20240 | | 7/1996 |
| WO | WO 99/09149 | * | 2/1999 |

OTHER PUBLICATIONS

M. S. Michael, M.M.E. Jacob, S.R.S. Probaharan ans S. Radhakrishna reported in Solid State Ionics 98 (1997) 167-174.

P.V. Wright investigated the electrical conductivities of various ionic complexes of poly(ethylene oxide) in Br. Polymer J. 7 (1975) 319-327.

G. G. Cameron, M.D. Ingram and K. Sarmouk, Eur. Polym. J. 26 (1990) 1097-1101).

Proceedings of the 2nd International Symposium of Solid Polymer (B. Scrosati (Ed)., Elsevier, Amsterdam, 1990, p. 49)).

T. Yamamoto, M. Inami and T. Kanbara in Chem. Mater. 5 (1994) 44-50.

X. Wei and D.F. Shriver in Chem. Mater. 10 (1998) 2307-2308.

F. Croce, S. D. Brown, S.G. Greenbaum, S.M. Slane and M. Salomon, Chem. Mater. 5 (1993) 1268-1272.

Polymer Electrolyte Reviews—1 and 2, J.R. MacCallum and C.A. Vincent (Elsevier, New York, 1987 and 1989).

Solid Polymer Electrolytes, Fundamentals and Technological Applications, F.M. Gray (VCH, New York, 1991).

Applications of Electroactive Polymers, B. Scrosati (Chapman and Hall, London, 1993).

Electrochemical Science and Technology of Polymers—1 and 2 R. G. Linford (Elsevier, London, 1987 and 1991).

Polymer Electrolytes, RSC Monographs, F.M. Gray (Royal Society of Chemistry, London, 1997) Chapter 1 & 2.

D. Fautex, Ph.D. Thesis, University of Quebec, 1986 and in the Proceedings of the 2nd International Symposium on Solid Polymer Electrolytes (B. Scrosati (Ed.), Elsevier, Amsterdam, 1990, p. 335).

Shell International B.V., The Hague—Search Report dated Sep. 15, 1998.

* cited by examiner

Variation of Conductivity with 1/T for Electrolytes based on the $(TMC)_n$ $LiCF_3SO_3$ System (n = 55 ■, 35 ●, 10 ◆, 9 □ and 7 ○)

Variation of Conductivity with 1/T for Electrolytes based on the $(TMC)_n LiClO_4$ System (n = 73 ✼, 43 ■, 23 ●, 10 ◆ and 2 ☐)

Conductivity Isotherms for $(TMC)_n$ $LiCF_3SO_3$ based Electrolytes (n = 40 ■, 55 ●, 70 ◆, and 85 °C □)

Conductivity Isotherms for $(TMC)_n$ $LiClO_4$ based Electrolytes (n = 40 ■, 55 ●, 70 ◆, and 85 °C □)

Effect of bis(2-ethylhexyl) sebacate upon the conductivity of a (TMC)$_9$ lithium triflate system ((a) 0 % (b) 5.3 % (c) 14.7 %)

Effect of diethyl phthalate upon the conductivity of a (TMC)$_9$ lithium triflate system ((a) 0 % (b) 10 %)

Effect of trimethylene carbonate upon the conductivity of a (TMC)9 lithium triflate system ((a) 0 % (b) 10 %)

Thermogravimetric Analysis of Polymer Electrolyte and Host Polymer samples a) $(TMC)_8$ $LiClO_4$, b) $(TMC)_{10}$ $LiCF_3SO_3$ and c) pure p(TMC)

Comparison of Temperatures of Onset of Weight Loss of Electrolytes Based on Lithium Perchlorate and Lithium Triflate Thermal Analysis of Polymer Electrolytes Based on (TMC)$_n$ LiCF$_3$SO$_3$ Thermal Analysis of Polymer Electrolytes Based on $(TMC)_n LiClO_4$

POLYMER ELECTROLYTE COMPOSITION

FIELD OF THE INVENTION

The present invention provides a composition for use as a polymer electrolyte, a process for preparing said composition, and its use, particularly in coulometers, displays, smart window, cells and batteries.

BACKGROUND OF THE INVENTION

Liquid electrolytes tend to suffer from problems relating to the loss of electrolyte from the cell case and require the use of cell seals. Under extreme conditions, for example during short circuit abuse of cells, the local heating within the cell case can lead to seal rupture, even with the most sophisticated seal and cell case design.

In general, solid electrolytes offer many advantages over liquid electrolytes such as more efficient use of space (no separator required), no risk of electrolyte spillage, simplification of seal design with resulting reduction of cost, extended temperature range of cell operation, better cathode operation and improved abuse resistance. Typical disadvantages of some solid electrolytes are that they tend to have a relatively low ionic conductivity and a poor mechanical compatibility with certain types of electrode materials.

Such electrolytes may be used in coulometers, smart windows or displays, cells and batteries.

During the last two decades a remarkable international research effort has been dedicated to studies in the domain of solvent-free solid polymer electrolytes based on lithium salts. For example, such research is discussed in Polymer Electrolyte Reviews—1 and 2, J. R. MacCallum and C. A. Vincent (Elsevier, New York, 1987 and 1989), Solid Polymer Electrolytes, Fundamentals and Technological Applications, F. M. Gray (VCH, New York, 1991), Applications of Electroactive Polymers, B. Scrosati (Chapman and Hall, London, 1993), Electrochemical Science and Technology of Polymers—1 and 2, R. G. Linford (Elsevier, London, 1987 and 1991) and Polymer Electrolytes, RSC Monographs, F. M. Gray (Royal Society of Chemistry, London, 1997).

The motivation for this research has been provided largely by the objective of developing novel lithium-based primary and secondary cells.

Advantages of polymer electrolytes typically include low processing costs, excellent mechanical properties, the possibility of using a large area/thin film format, variable cell configuration, low device weight, good chemical stability, good thermal stability and access to lithium chemistry.

However, whilst polymer electrolytes offer several important advantages over conventional liquid non-aqueous systems, the first generation of lithium ion conducting solvent-free polymer electrolytes also suffered from severe drawbacks.

Poly(ethylene oxide) (PEO) was the first polymer in which salt solubilisation and ionic transport were recognised.

D. E. Fenton, J. M. Parker and P. V. Wright reported the preparation of crystalline complexes of sodium and potassium salts with poly(ethylene oxide) in Polymer 14 (1973) 589.

P. V. Wright investigated the electrical conductivities of various ionic complexes of poly(ethylene oxide) in Br. Polymer J. 7 (1975) 319-327.

Poly(ethylene oxide) is still the most thoroughly characterised electrolyte host matrix today. However, in spite of the promise of initial results, systems based on poly(ethylene oxide) were found to crystallise as salt-polymer complexes or free polymer, resulting in a less favourable conductivity behaviour in certain ranges of salt concentrations and over a critical range of operating temperatures.

During the years which followed the introduction of the solid polymer electrolyte (essentially solvent-free systems) a remarkable number of different polymer hosts were studied, and, surprisingly it was soon widely accepted that the most effective host polymer structure was in fact the $CH_2CH_2O$ group. Whilst the capacity of this group to co-ordinate guest species is exceptional, high molecular weight samples crystallise with a significant reduction in the observed conductivity.

It has been found that ion conductivity is confined to the amorphous domains of a polymer electrolyte and that the tendency of the polymer electrolyte to crystallise results in difficulties in the reproducible preparation of electrolytes (G. G. Cameron, M. D. Ingram and K. Sarmouk, Eur. Polym. J. 26 (1990) 1097-1101).

Various strategies have been applied to attenuate the disadvantages of electrolytes based on the $CH_2CH_2O$ structural unit and electrolytes containing many different salts, polymer architectures and plasticising additive formulations have been reported and reviewed, for example in Polymer Electrolytes, RSC Monographs, as cited previously herein.

Recently, a new strategy has been proposed by T. Yamamoto, M. Inami and T. Kanbara in Chem. Mater. 6 (1994) 44-50, and by X. Wei and D. F. Shriver in Chem. Mater. 10 (1998) 2307-2308, based on the use of relatively rigid polymer hosts with comparatively high values of glass transition temperature, Tg.

Yamamoto et al. describe the preparation and properties of polymer solid electrolytes based on poly(vinyl alcohol) (PVA) and poly[arylene(1,3-imidazolidene-2,4,5-trione-1,3-diyl)] (poly(parabamic acid), PPA).

Wei et al. describe two rigid polymer systems of poly (vinylene carbonate) (PVIC) (I) and poly(1,3-dioxolan-2-one-4,5-diyl oxalate) (PVICOX) (II) for the preparation of polymer electrolytes. The systems are said to display both favourable conductivity and mechanical properties.

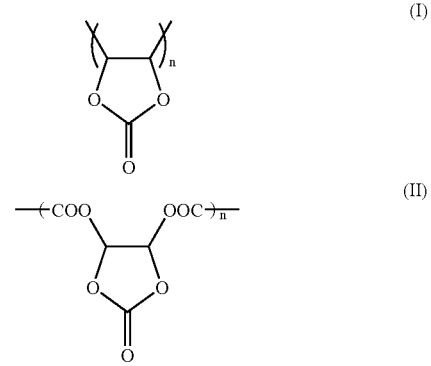

The conductivities of the PVICOX system (II) are shown to be about 2-4 orders of magnitude higher than those of the PVIC system (I).

Wei et al. hypothesise that this is due to the irregularity of the PVICOX system (II) which frustrates close packing, thereby increasing static free volume and conductivity.

The developments of Yamamoto et al. and Wei et al. seem to go against the accepted precepts of polymer electrolyte operation. However, surprisingly high conductivities have been reported.

Although many other polymer architectures have been assessed as host polymers, prior to the publication of the results reported by Yamamoto et al., the ethylene oxide unit was widely believed to be the best option for high ionic conductivity as a consequence of its unique combination of structural and thermodynamic factors.

The results obtained by Yamamoto et al. and Wei et al. confirm that even polymers which do not contain the ethylene oxide structural unit may be effective media for the dissolution and efficient transport of charged species.

It has been shown in the art that the introduction of small polar molecules into the polymer network often results in a marked improvement in the observed ionic conductivity of the polymer.

Cameron et al., as previously cited herein, noted a decrease in viscosity and an increase in conductivity when 10 wt. % of the plasticisers tetrahydrofuran (THF) or propylene carbonate (PC) were added to poly(tetrahydrofuran) (PTHF) and to a copolymer of ethylene oxide and propylene oxide (50:50 by weight).

R. Huq, R. Koksbang, P. E. Tonder and G. C. Farrington reported the results of a study on the effect of a mixed plasticiser on the conductivities and the physical/chemical properties of radiation-polymerised polyether electrolytes. The mixed plasticiser compositions of ethylene carbonate and propylene carbonate containing 1M lithium hexafluoroarsenate (V) ($LiAsF_6$) were found to possess better thermal, mechanical and lithium cycling properties.

M. S. Michael, M. M. E. Jacob, S. R. S. Probaharan and S. Radhakrishna reported in Solid State Ionics 98 (1997) 167-174 that a novel class of esters of benzene-1,2-dicarboxylic acids such as dioctyl phthalate (DOP), dibutyl phthalate (DBP) and dimethyl phthalate (DMP) had been used as plasticisers in high molecular weight PEO-lithium perchlorate matrix to improve the room temperature ionic conductivity of polymer-salt complex.

Although this improvement in conductivity in certain electrolyte systems has been interpreted in terms of an alteration in the transport mechanism (F. Croce, S. D. Brown, S. G. Greenbaum, S. M. Slane and M Salomon, Chem. Mater. 5 (1993) 1268-1272) or plasticisation of the polymer structure (Cameron et al. as cited previously herein), other effects may also contribute.

There has now been found a novel class of polymer electrolytes based on polymers that possess good ionic conductivity and excellent mechanical properties.

SUMMARY OF THE INVENTION

The present invention provides a composition for use as a polymer electrolyte, which composition comprises one or more polar materials and one or more polyesters of formula III, $$-\!\!+\!\!A\!\!+_y\quad\quad\text{(III)}$$

wherein y is from 1.5 to 80 and each unit A may be identical or different and is of the structure IV, $$-\!\!O\!\!-\!\!\overset{\overset{O}{\|}}{C}\!\!-\!\!O\!\!-\!\!(\!B\!)_x\!\!-\quad\quad\text{(IV)}$$

wherein x is from 1 to 5 and each unit B may be identical or different and is of the structure V, $$-\!\!\overset{\overset{R}{|}}{\underset{\underset{R^1}{|}}{C}}\!\!-\quad\quad\text{(V)}$$

wherein R and $R^1$ are each, independently, hydrogen, an optionally substituted hydrocarbyl group or an inert functional group.

BRIEF DESCRIPTION OF THE DRAWINGS

The present invention will now be illustrated by the following Examples, which should not be regarded as limiting the scope of the present invention in any way.

DETAILED DESCRIPTION OF THE INVENTION

Figure 1:
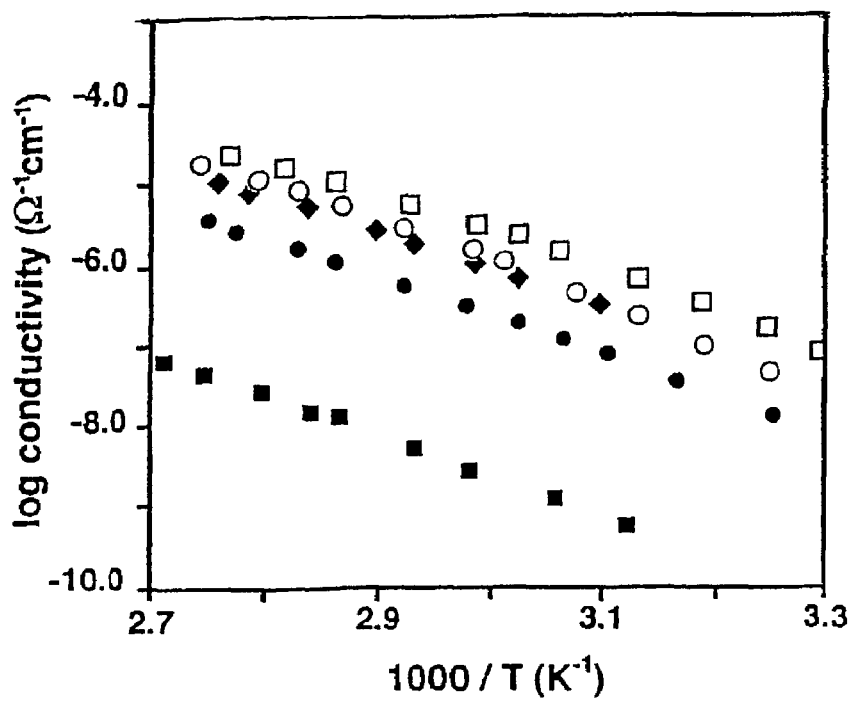
FIG. 1 shows the variation of conductivity with reciprocal temperature for polymer electrolytes based on a (TMC)n lithium triflate system.

By "polar materials" in the present invention is meant salts and proton conductor systems. Typical proton conductor systems include phosphoric acid and sulphamide.

By "hydrocarbyl group" in the present invention is meant a group containing only carbon and hydrogen. Unless otherwise stated, the number of carbon atoms is preferably from 1 to 4. Examples of hydrocarbyl groups include methyl, ethyl and propyl.

In the present invention, the phrase "optionally substituted hydrocarbyl" is used to describe hydrocarbyl groups optionally containing one or more "inert" heteroatom-containing functional groups. By "inert" is meant that the functional groups do not interfere to any substantial degree with the ionic conductivity and/or mechanical properties of the resulting composition. Said inert groups may include ethers and polyethers. Such inert groups may act as plasticisers. Non-limiting examples of such inert groups are —CH$_2$CH$_2$OCH$_3$ and —CH$_2$CH$_2$OCH$_2$CH$_2$OCH$_3$.

Inert functional group: a group other than optionally substituted hydrocarbyl which is inert under the process conditions. By "inert" is meant that the functional group does not interfere to any substantial degree with the ionic conductivity and/or mechanical properties of the resulting composition.

Compositions according to the present invention generally comprise polyesters having a weight average molecular weight, $M_W$, greater than 30,000, preferably greater than 75,000, and more preferably greater than 250,000.

The weight average molecular weight, $M_W$, of the polyester may be determined by several techniques which give closely similar results. $M_W$ may be easily determined by gel permeation chromatography (GPC) with calibration of the polyester as will be appreciated by those skilled in the art. Alternatively, $M_W$ may be determined by light scattering, as described in ASTM D 4001-93.

Said polyesters generally have a glass transition temperature, Tg, in the range of from −60 to 20° C., preferably in the range of from −50 to 10° C., and more preferably in the range of from −30 to 5° C.

Polyesters according to the present invention are generally polymers of carbonic acid made by the condensation polymerisation of one or more different polyhydridic alcohols with phosgene or derivatives thereof. Said polyesters may also be formed by the ring opening polymerisation of a cyclic carbonate as described previously in the art or by transesterification with dialkylcarbonate or alkylene carbonate.

Polyhydric alcohols that may be used in the preparation of said polyesters include 1,2-ethanediol, 1,3-propanediol, 1,4-butanediol, 1,5-pentanediol, 1,6-hexanediol, 2-methyl-1,3-propanediol, 2,2-dimethyl-1,3-propanediol, trimethylolethane, glycerine and pentaerythritol.

The preferred polyesters in respect of the present invention are poly(trimethylene carbonate) and esters of other polyhydric alcohols described above.

The amount of polyester incorporated in the composition is generally in the range of from 50 to 99 wt. %, preferably in the range of from 60 to 94 wt. %, and more preferably in the range of from 65 to 83 wt. % based on the composition.

The amount of polar material incorporated in the composition is generally in the range of from 50 to 1 wt. %, preferably in the range of from 40 to 6 wt. %, and more preferably in the range of from 35 to 17 wt. % based on the composition.

The composition of the present invention may comprise salts such as quaternary ammonium salts for example ammonium thiocyanate and/or metal salts.

Metal salts that may be generally employed in the composition of the present invention include those wherein the metal is selected from lithium, sodium, potassium, nickel, zinc, silver and lanthanides such as neodymiun, europium, erbium and thulium.

In particular, triflate, perchlorate, bromide, chloride, iodide, bis(trifluoromethylsulphonyl)imide, tetrafluoroborate, trifluoromethanesulphonate, hexafluoroarsenate (V), thiocyanate, acetate, dichlorosulphonimide, fluorochlorosulphonimide, sulphonate and tetrachloroaluminate salts of the above-mentioned metals are preferred.

According to the present invention, preferred metal salts are lithium metal salts.

Particularly preferred lithium metal salts are lithium triflate, lithium perchlorate, lithium bromide, lithium chloride, lithium iodide, lithium bis(trifluoromethylsulphonyl) imide, lithium tetrafluoroborate, lithium trifluoromethanesulphonate, lithium hexafluoroarsenate (V), lithium thiocyanate, lithium acetate, lithium dichlorosulphonimide, lithium fluorochlorosulphonimide, lithium sulphonate and lithium tetrachloroaluminate.

Compositions may be prepared with a range of salt concentrations by adding different quantities of the salt to the composition. The composition of the resulting mixture may be identified by indicating the value of n. In this context, n is the molar ratio of monomer units per mole of added salt. Generally, n is in the range of from 1 to 100, preferably in the range of from 1 to 80, more preferably in the range of from 1 to 15 and most preferably in the range of from 1 to 5.

In a preferred embodiment of the present invention, the composition is a solid, that is to say, the polymer electrolyte is a solid, solvent-free polymer electrolyte.

However, in another aspect of the present invention, the composition may further comprise a solvent. Thus, the polyester may act as an immobiliser to a non-aqueous electrolyte of a salt in a solvent, for example, lithium tetrafluoroborate, lithium perchlorate, lithium hexafluoroarsenate, lithium tetrachloroaluminate and /or lithium bromide in acetonitrile, propylene carbonate, dimethylsulphoxide (DMSO), etc.

The composition according to the present invention may further comprise one or more plasticiser compounds.

Said plasticiser compounds may be typically selected from propylene carbonate, ethylene carbonate, dimethylsulphoxide, dioctyl phthlate, dibutyl phthalate, diethyl phthalate, dimethyl phthalate, butyrolactone, dimethyl carbonate, diethyl carbonate, bis(2-ethylhexyl) sebacate and/or trimethylene carbonate.

Plasticisers may be typically used at doping levels in the range of from 1 to 50 wt. %, preferably in the range of from 1 to 20 wt. % and more preferably in the range of from 5 to 15 wt. %.

Compositions according to the present invention may be prepared by weighing out polyester and salt components and adding a volume of solvent to produce a solution comprising a homogeneous mixture of the components. Said solution may be quite viscous in character.

In a preferred embodiment of the present invention, the solvent of said solution may be allowed to evaporate under an inert atmosphere. Such a procedure typically allows the formation of a thin flexible film of the composition.

Solvents that may be typically used in the formation of compositions according to the present include dry tetrahydrofuran, dry acetonitrile, dry methanol and dry ethanol.

The inert atmosphere that is typically employed in the formation of compositions according to the present invention may include dry argon, dry nitrogen, or dry helium.

In another embodiment of the present invention, the composition may be prepared by polymerising polyester monomers in situ in the presence of the salt.

Compositions according to the present invention may be used as polymer electrolytes in coulometers, displays, smart windows, cells and batteries. The present invention therefore also provides a cell and/or battery comprising said composition.

By "smart window" is meant a variable transmission device wherein the transmission of light through the device may be controlled electrochemically, darkening a thin anode or cathode on the inner surface of the glass layer of the window.

EXPERIMENTAL SECTION

1. Materials

Poly(trimethylene carbonate) (p(TMC)) with a molecular weight of $3.2 \times 10^5$ was prepared by catalysed bulk polymerisation and characterised by gel permeation chromatography (GPC). The polymer was a very flexible elastomer and was dried before use at 65° C., under vacuum, for a period of about 7 days.

Lithium triflate (95%, ex. Aldrich) and lithium perchlorate (99.99%, ex. Aldrich) were dried under vacuum at 180 and 150° C. respectively, for 7 days and then stored in a high integrity, dry argon-filled glovebox.

All subsequent sample preparations, manipulations of salt and measurements were carried out under a dry argon atmosphere.

Unless otherwise stated, solvent grades employed herein were purchased ex. Aldrich and were anhydrous, purity 99.9%, inhibitor free and packaged under argon.

2. Sample Preparation

Homogeneous solutions of p(TMC) and lithium triflate or lithium perchlorate in tetrahydrofuran (THF) were prepared by adding known weights of p(TMC) and the appropriate lithium salt to a convenient volume of solvent and stirring the components within a dry argon-filled preparative glovebox.

The resulting solutions were cast into glass rings on glass plates and the solvent was then removed slowly by locating the moulds in an isolated chamber within the preparative glovebox. The atmosphere of the chamber was re-circulated through a column of molecular sieves to effect a slow evaporation and to form films of about 150 μm thickness. These films were dried at 65° C. under vacuum for 3 days to remove residual solvent.

3. Measurements

Total ionic conductivities of electrolyte samples were determined using a constant volume support with gold blocking electrodes located within a Buchi TO 150 oven.

The sample was measured with a type K thermocouple placed close to the electrolyte film and impedance measurements were carried out with a Solartron 1250 Frequency Response Analyser and 1286 Electrochemical Interface, between 25 and 100° C. Measurements of conductivity were effected during heating cycles and at temperature intervals of about 7° C. The reproducibility of conductivities obtained in initial and subsequent heating cycles was extremely good and taken as confirmation of the efficiency of the support operation and mechanical stability of the samples.

Polymer electrolyte film sections were subjected to thermal analysis under a flowing argon atmosphere between −40 and 350° C. and at a heating rate of 5 deg.min$^{-1}$ using a Mettler TC11 controller and a DSC 20 oven. Samples in the form of disks were cut from polymer films and presented for analysis in 40 μl aluminium cans with perforated lids.

Samples for thermogravimetric studies were also prepared by cutting sections of suitable dimensions from electrolyte films. These sections were transferred to open platinum crucibles and analysed using a Rheometric Scientific thermobalance operating under an argon atmosphere. A heating rate of 5 deg.min$^{-1}$ was used to analyse all the electrolyte samples.

4. Results and Discussion (i) Ionic Conductivity

The total ionic conductivity of electrolytes with a range of composition, based on lithium perchlorate and lithium triflate were studied.

Figure 2:
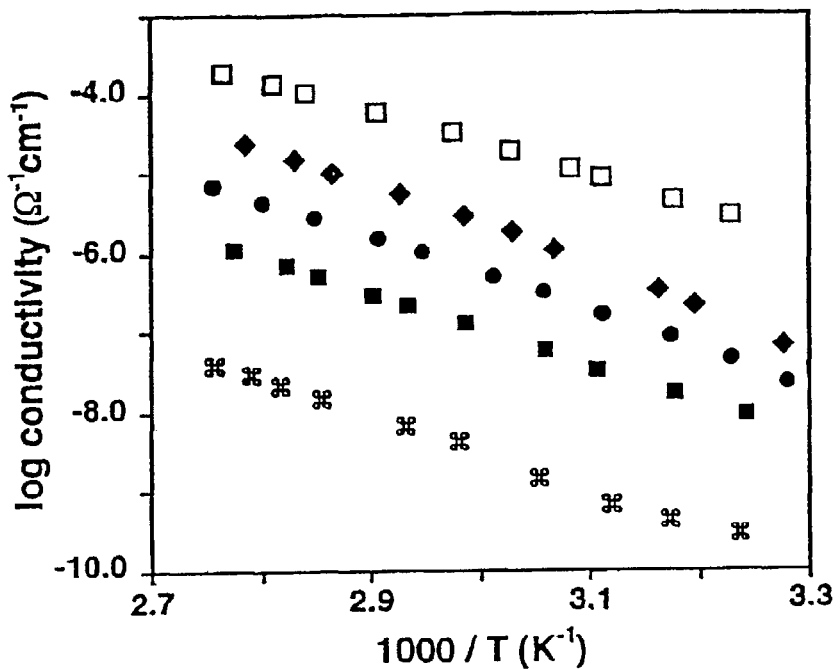
FIG. 2 shows the variation of conductivity with reciprocal temperature for polymer electrolytes based on a (TMC)n lithium perchlorate system.

The results of conductivity measurements on various compositions within a series of electrolyte films with compositions of lithium triflate and lithium perchlorate with values of n from 2 to 73 are illustrated in FIGS. 1 and 2, respectively.

Over the entire range of compositions, and in both systems, the variation of conductivity with reciprocal temperature was found to be linear within experimental error with no breaks or inflections. The highest conductivity in the lithium triflate-based electrolyte system was recorded at a composition with n close to 9. In contrast, the conductivity of electrolytes based on lithium perchlorate electrolytes continued to increase with concentration up to values of n of 2.

The activation energy of the ion transport through the polymer medium, assuming linear behaviour, was approximately 40 kJ.mol$^{-1}$, with a variation of less than 7% over the composition range studied, suggesting that the properties of the polymer host determine the ion transport, not the nature of the guest salt species.

Figure 3:
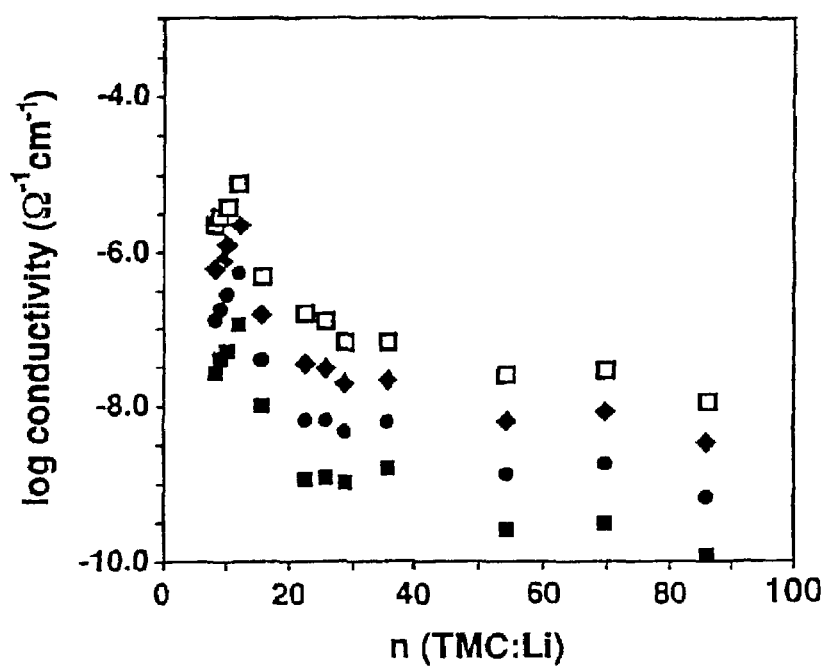
FIG. 3 shows conductivity isotherms for polymer electrolytes based on a (TMC)n lithium triflate system.
Figure 4:
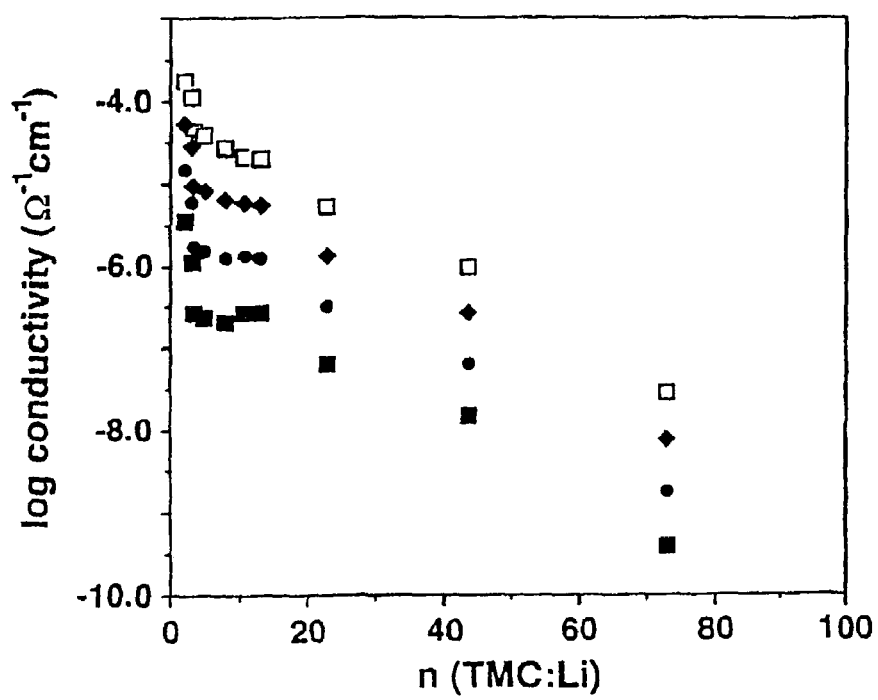
FIG. 4 shows conductivity isotherms for polymer electrolytes based on a (TMC)n lithium perchlorate system.

The effect of guest salt concentration on total ionic conductivity can be clearly seen in FIGS. 3 and 4.

These results show the substantial variation of total ionic conductivity with the concentration of the guest salt species (lithium triflate or lithium perchlorate) is greater than that found with "conventional" electrolytes based on solvent-free PEO-based systems such as those described by D. Fauteux, Ph.D. Thesis, University of Quebec, 1986 and in the Proceedings of the 2$^{nd}$ International Symposium on Solid Polymer Electrolytes (B. Scrosati (Ed.), Elsevier, Amsterdam, 1990, p. 235).

In the lithium triflate-based electrolyte, the gradual increase in the conductivity with the salt concentration and the number of charge carriers available suddenly alters at about n=20. From this composition to n=9, the conductivity rises to a maximum and then falls rapidly in electrolytes with greater salt content. This sudden decrease in conductivity is fairly common in solvent-free polymer electrolyte systems and is normally explained in terms of an increase in the number of polymer-salt interactions resulting in restrictions in the mobility of the polymer chain segments which is responsible for ion transport.

Although the density of charge distribution over triflate and perchlorate anions is similar, the total ionic conductivity observed in the art with lithium perchlorate-based polymer electrolytes is generally greater than that of those containing triflate ions at a similar concentration.

This behaviour is also apparent in the p(TMC)-based systems studied herein. No phase separation was observed in electrolytes doped with lithium perchlorate, even at compositions close to n=2, in contrast to the triflate-based electrolytes which reach a solubility limit at about n=5. At close to n=2, the lithium perchlorate-containing electrolyte showed a maximum conductivity of approximately $3 \times 10^{-4} \Omega^{-1}$ cm$^{-1}$.

As may be confirmed by reference to FIG. 4, the total ionic conductivity of lithium perchlorate-based p(TMC) electrolytes continues to increase with salt concentrations to very high compositions of added salt.

The p(TMC) polymer, as an amorphous, polar macromolecular host, is a more suitable solvent for the preparation of polymer electrolytes than PEO. Even without additives, the electrolytes display encouraging levels of performance which may be further improved with the use of suitable free-volume enhancing components.

Studies have shown significant improvement in the total ionic conductivity of the p(TMC) as a result of the use of even fairly low quantities of plasticiser.

A series of electrolytes based on a constant lithium triflate concentration was prepared with the inclusion of a plasticiser molecule in the casting solution.

Figure 5:
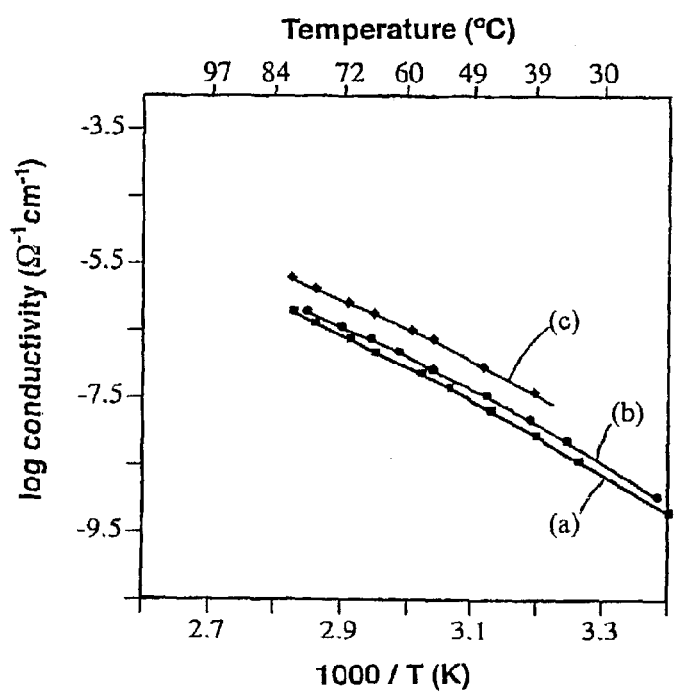
FIG. 5 shows the effect of bis(2-ethylhexyl) sebacate upon the conductivity of a $(TMC)_9$ lithium triflate system.
Figure 6:
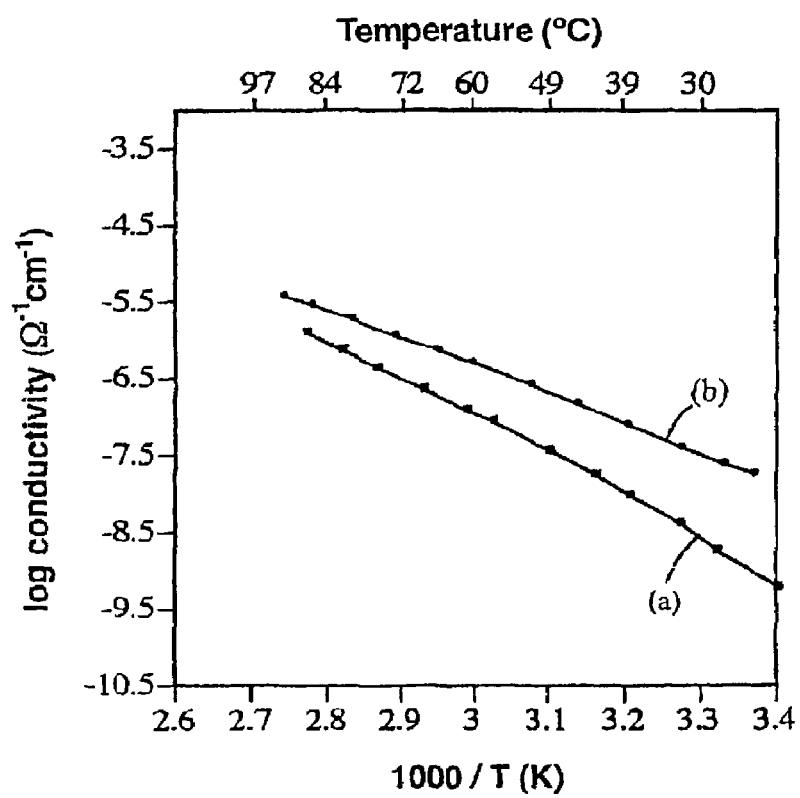
FIG. 6 shows the effect of diethyl phthalate upon the conductivity of a $(TMC)_9$ lithium triflate system.
Figure 7:
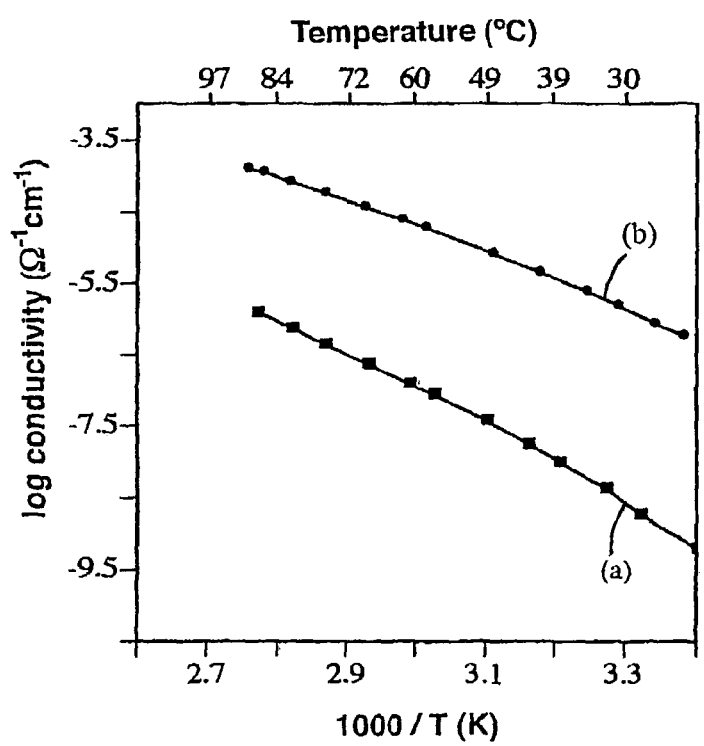
FIG. 7 shows the effect of trimethylene carbonate upon the conductivity of a $(TMC)_9$ lithium triflate system.

Plasticisers bis(2-ethylhexyl) sebacate, diethyl phthalate and trimethylene carbonate were used at doping levels of between 5 and 15 wt. %. As expected, the presence of plasticiser increased the ionic conductivity (FIGS. 5 to 7). However, at doping levels of greater than about 15 wt. %, the mechanical properties began to degrade and the material became gel-like.

Trimethylene carbonate was found to be an efficient conductivity enhancer without decreasing the mechanical robustness of the electrolyte film.

(ii) Thermal Analysis

The results of thermal analysis of samples of polymer electrolyte according to the present invention are illustrated in FIGS. 8 to 11.

Studies of the thermal behaviour of electrolytes based on both lithium perchlorate and lithium triflate showed a glass transition at about −18° C. which was almost unaffected by the salt content between n of 85 and about 15.

As the salt content is further increased to values of n less than about 15, a slight shift of Tg to higher temperatures is perceptible.

This suggests that significant interaction between the guest ionic species and the polymer host chains only takes place at these higher concentrations of lithium salt. No fusion of polymer-salt complexes or uncomplexed polymer is apparent in any of the electrolytes studied and no other thermal events are observed until temperatures of about 200° C. when an endothermic peak likely to be due to polymer decarboxylation is registered.

Figure 8:
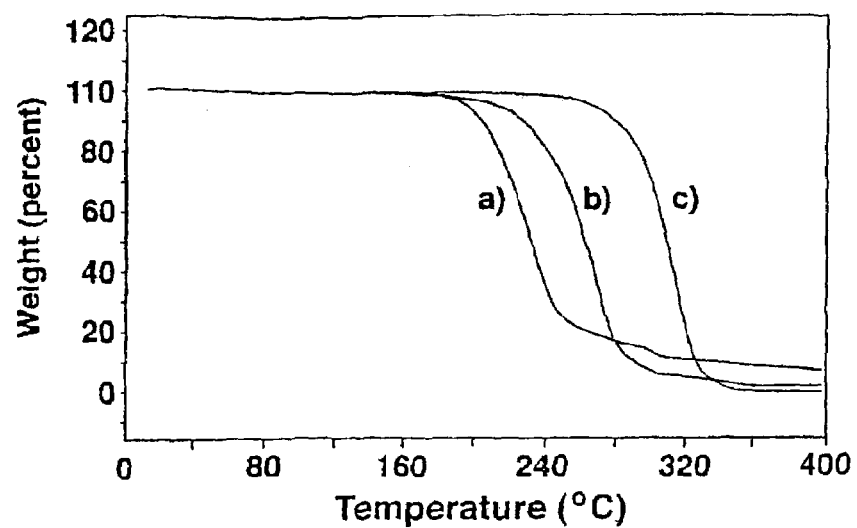
FIG. 8 shows thermogravimetric analysis of pure p(TMC) and polymer electrolytes based on a (TMC)n lithium perchiorate system and a (TMC)n lithium triflate system.

The results of thermogravimetric studies are consistent with this interpretation and the thermograms of pure polymer, and electrolytes containing high concentrations of lithium perchlorate or lithium triflate are illustrated in FIG. 8.

In accordance with results previously observed with PEO-based electrolytes (Proceedings of the $2^{nd}$ International Symposium on Solid Polymer (B. Scrosati (Ed.), Elsevier, Amsterdam, 1990, p. 49).), the onset of the degradation process is dependent upon electrolyte composition, confirming that the salt has a destabilising influence upon polymer host.

Figure 9:
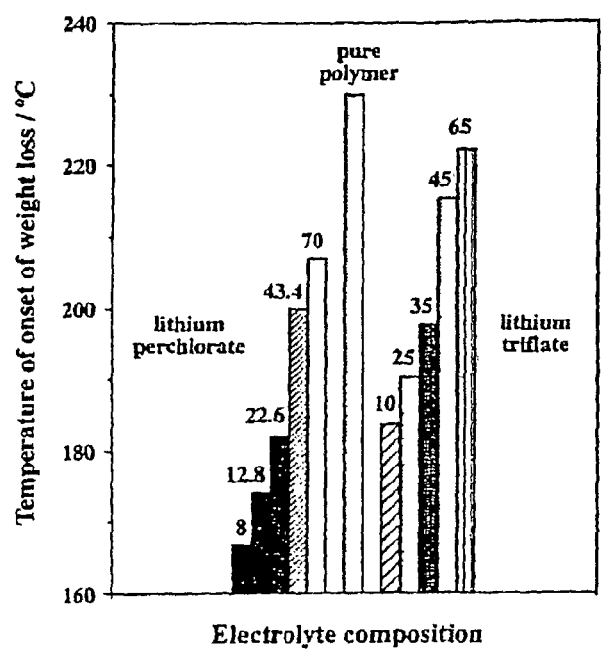
FIG. 9 shows a comparison of temperatures of onset of weight loss of electrolytes based on lithium perchlorate and lithium triflate.
Figure 10:
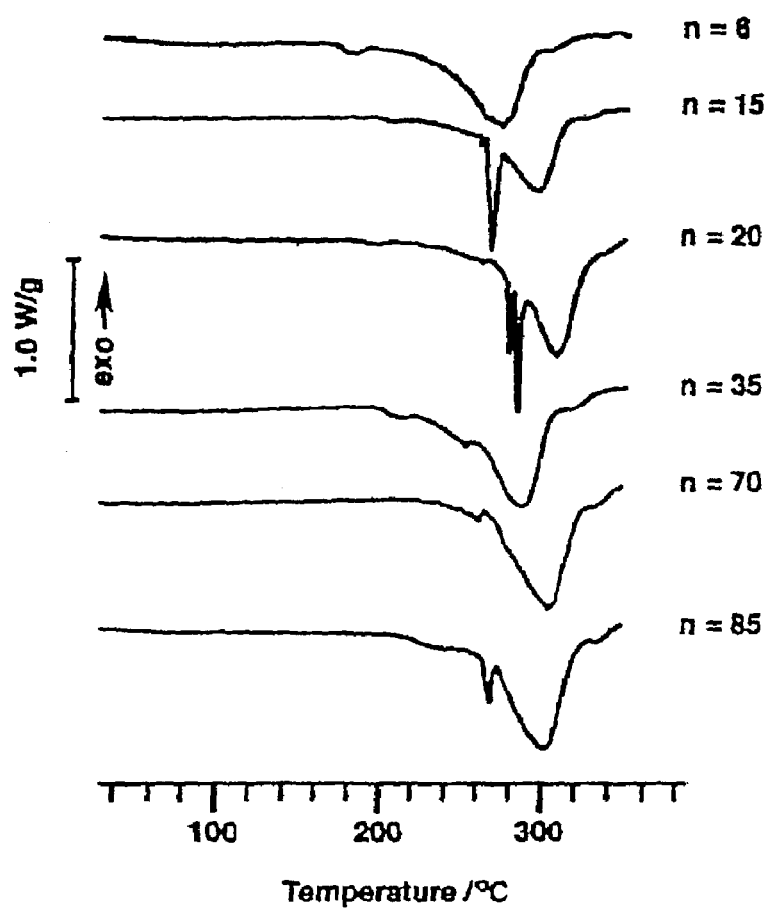
FIG. 10 shows thermal analysis of polymer electrolytes based on a (TMC)n lithium triflate system.
Figure 11:
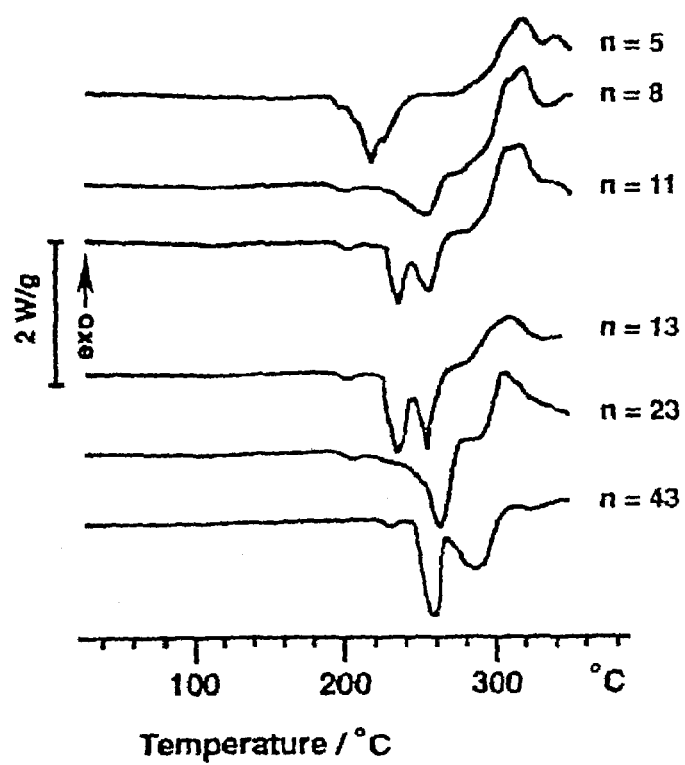
FIG. 11 shows thermal analysis of polymer electrolytes based on a (TMC)n lithium perchlorate system.

As can be seen from FIG. 9, the pure host polymer p(TMC) began to degrade thermally at a temperature close to 230° C. Polymer electrolytes with values of n between 85 and 2 were found to be less thermally stable than the pure polymer. Electrolytes with high concentrations of lithium perchlorate were found to degrade at about 160° C. while lithium triflate-based materials were stable to approximately 180° C. These thermal stabilities are considered to be adequate for applications of the electrolytes in cells or batteries operating at low or moderate temperatures.

As this effect of guest ionic species has been interpreted as a consequence of the interaction between the guest ions and the polymeric solvent, weakening the bonds within the macromolecular backbone, this observation also suggests that the interaction between the guest salt and the host polymer increases with the salt content.

Lithium perchlorate-containing electrolytes show thermal behaviour which is similar to that observed with lithium triflate-based films at low temperatures, but with a completely different degradation thermogram. As may be confirmed by reference to FIGS. 10 and 11, while the onset of the perchlorate degradation is similar to the process observed with the triflate, once initiated, the electrolyte samples suffer a strongly exothermic process, the intensity of which is dependent on the amount of salt present in the sample The electrolytes formed with high lithium salt compositions (up to n=2) for lithium perchlorate-based material were obtained as transparent, flexible films.

These materials have mechanical properties which are suitable for application in primary or secondary cells or batteries which suffer from anode or cathode expansion during cell discharge or re-charge. The polymer electrolyte, being mechanically flexible will adapt to such changes in electrode dimension, maintaining ionic contact with the electrode material.

In conclusion, a new host polymer matrix based on polyester rather than polyether coordinating units, with lithium triflate and lithium perchlorate guest species, has been used to form solvent-free electrolytes.

The highest ionic conductivity observed with these new electrolytes at a salt-rich composition, is similar or better than that observed in many other solvent and additive-free systems.

The results of thermal analysis have confirmed that polymer electrolytes based on this host matrix are completely amorphous. All electrolyte samples showed adequate windows of thermal stability for practical devices.

We claim:

1. A composition for use as a polymer electrolyte comprising one or more polar materials and one or more polyesters of formula III,

(III)

wherein y is from 1.5 to 80 and each unit A may be identical or different and is of the structure IV,

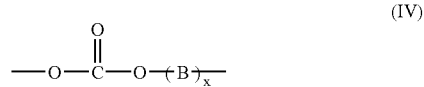

(IV)

wherein x is from 1 to 5 and each unit B may be identical or different and is of the structure V,

(V)

wherein R and $R^1$ are each, independently, hydrogen, optionally substituted hydrocarbyl or an inert functional group, wherein the one or more polar materials are present in the composition in an amount of from 6 to 50 wt. % of the composition and the one or more polyesters of formula (III) are present in the composition in an amount of from 50 to 99 wt.%; and wherein at least one of the one or more polar materials is a salt or a proton conductor system, where the salt is selected from the group consisting of quaternary ammonium salts, ammonium thiocyanate salts, and triflate, perchlorate, bromide, chloride, iodide, bis(trifluoromethylsulphonyl)imide, tetrafluoroborate, trifluoromethanesulphonate, hexafluoroarsenate (V), thiocyanate, acetate, dichlorosulphonimide, fluorochlorosulphonimide, sulphonate and tetrachloroaluminate salts of lithium, sodium, potassium, nickel, zinc, silver, and lanthanides, and where the proton conductor system is selected from phosphoric acid or sulphamide; and wherein the composition is amorphous.

2. The composition of claim 1 wherein said polyesters have a weight average molecular weight greater than 30000.

3. The composition of claim 1 wherein said composition is a solid.

4. The composition of claim 1 wherein the composition further comprises one or more plasticizer compounds.

5. A composition for use as a polymer electrolyte comprising one or more polar materials and one or more polyesters of carbonic acid and a polyhydric alcohol which is selected from the group consisting of 1,2-ethanediol, 1,3-propanediol, 1,4-butanediol, 1,5-pentanediol, 1,6-hexanediol, 2-methyl-1,3-propanediol, and 2,2-dimethyl-1,3-propanediol, wherein the polyesters have a weight average molecular weight greater than 30000, wherein the one or more polar materials are present in the composition in an amount of from 6 to 50 wt. % of the composition and the one or more polyesters are present in the composition in an amount of from 50 to 99 wt.%; and wherein at least one of the one or more polar materials is a salt or a proton conductor system, where the salt is selected from the group consisting of quaternary ammonium salts, ammonium thiocyanate salts, and triflate, perchlorate, bromide, chloride, iodide, bis(trifluoromethylsulphonyl)imide, tetrafluoroborate, trifluoromethanesulphonate, hexafluoroarsenate (V), thiocyanate, acetate, dichlorosulphonimide, fluorochlorosulphonimide, sulphonate and tetrachloroaluminate salts of lithium, sodium, potassium, nickel, zinc, silver, and lanthanides, and where the proton conductor system is selected from phosphoric acid or sulphamide; and wherein the composition is amorphous.

6. The composition of claim 5 wherein the polyester is poly(trimethylene carbonate).

7. The composition of claim 5 wherein said composition is a solid.

8. The composition of claim 5 wherein the composition contains one or more plasticiser compounds.

9. The composition of claim 5 wherein the polyesters have a weight average molecular weight greater than 75000.

10. The composition of claim 9 wherein the polyesters have a weight average molecular weight greater than 250000.

* * * * *